(12) United States Patent
Hiller

(10) Patent No.: US 10,074,259 B2
(45) Date of Patent: *Sep. 11, 2018

(54) SYSTEM AND METHOD FOR LOCATING A PATIENT

(71) Applicant: ALLSCRIPTS SOFTWARE, LLC, Chicago, IL (US)

(72) Inventor: Dean Hiller, Shrub Oak, NY (US)

(73) Assignee: Allscripts Software, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/640,986

(22) Filed: Jul. 3, 2017

(65) Prior Publication Data
US 2018/0025606 A1 Jan. 25, 2018

Related U.S. Application Data

(63) Continuation of application No. 15/212,561, filed on Jul. 18, 2016, now Pat. No. 9,697,715, which is a continuation of application No. 14/690,735, filed on Apr. 20, 2015, now Pat. No. 9,398,407, which is a continuation of application No. 13/840,074, filed on Mar. 15, 2013, now Pat. No. 9,013,299.

(60) Provisional application No. 61/786,249, filed on Mar. 14, 2013.

(51) Int. Cl.
G08B 1/08 (2006.01)
G08B 21/02 (2006.01)
G06K 7/10 (2006.01)
G06F 19/00 (2018.01)
H04W 4/02 (2018.01)
G06K 19/07 (2006.01)
H04L 1/00 (2006.01)
G06F 1/00 (2006.01)
G06Q 50/22 (2018.01)

(52) U.S. Cl.
CPC ..... *G08B 21/0275* (2013.01); *G06F 19/3418* (2013.01); *G06K 7/10366* (2013.01); *G06K 19/0723* (2013.01); *H04W 4/02* (2013.01); *G06F 1/00* (2013.01); *G06Q 50/22* (2013.01); *H04L 1/00* (2013.01)

(58) Field of Classification Search
CPC ..................................... G06F 1/00; H04L 1/00
See application file for complete search history.

(56) References Cited

U.S. PATENT DOCUMENTS

2008/0164998 A1* 7/2008 Scherpbier ............. G06Q 10/06
340/539.13
2012/0010901 A1* 1/2012 Johnson ................ G06F 19/327
705/2

* cited by examiner

Primary Examiner — Shirley Lu
(74) Attorney, Agent, or Firm — Medley, Behrens & Lewis, LLC

(57) ABSTRACT

A method for tracking a patient in a medical facility is disclosed. The method includes determining whether a patient is to be moved, indicating the time at which the patient should start to be moved, and interrogating a RFID sensor on the patient at a predetermined time interval to determine when the patient has been moved.

16 Claims, 2 Drawing Sheets

US 10,074,259 B2

SYSTEM AND METHOD FOR LOCATING A PATIENT

CROSS-REFERENCE TO RELATED APPLICATION

The present application incorporates by reference U.S. patent application Ser. Nos. 14/690,735; 13/840,074; 61/786,249; any patent application publication of each of the foregoing; and any patent issuing from each of the foregoing.

COPYRIGHT STATEMENT

All of the material in this patent document, including the computer program listing, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

FIELD OF THE INVENTION

The present invention is related to healthcare. More specifically, the present invention relates to bed management.

BACKGROUND OF THE INVENTION

Patient/bed management has become an important aspect of hospital management. Ensuring that the right patient is getting the right testing and treatment is a major reason for this. Protection against administering the wrong medicines and missed diagnosis as a result of a failure by a patient facility is paramount in eliminating accidents.

Currently, there are bed management systems, such as the graphical bed management system disclosed in U.S. Pat. No. 7,774,215. There are also material tracking systems, for example, the RFID material tracking system disclosed in U.S. Pat. No. 8,125,316. Unfortunately, systems such as these are unable to determine the location of patients or determine when a patient should be transported to and from a treatment, for example.

Accordingly, there exists a need for an improved system for tracking patients/beds in a medical facility.

SUMMARY OF THE INVENTION

The present invention includes many aspects and features. Moreover, while many aspects and features relate to, and are described in, the context of healthcare, the present invention is not limited to use only in this context, as will become apparent from the following summaries and detailed descriptions of aspects, features, and one or more embodiments of the present invention.

Accordingly, one aspect of the present invention relates to a method for tracking a patient in a medical facility. The method includes determining whether a patient is to be moved, indicating the time at which the patient should start to be moved, and interrogating a RFID sensor on the patient at a predetermined time interval to determine when the patient has been moved.

In a feature of this aspect, the method further includes: determining the time it takes to move the patient to a receiving location; determining whether the patient will reach the receiving location when scheduled; and/or displaying the location of the patient based on the interrogation of the RFID sensor.

In a further feature of this aspect the method includes: determining transport times to move from a point A in the medical facility to a point B in the medical facility: scheduling a patient move based on the transport times; and/or scheduling a transporter to move patient based on the transport times. In a further feature of this aspect the method includes interrogating the RFID sensor on the patient periodically throughout the day to confirm the location of the patient in the medical facility.

Broadly defined, the present invention according to one aspect is or relates to a system for tracking a patient in a medical facility including: a plurality of RFID readers for sensing the presence of an RFID sensor on a patient, and periodically providing patient tracking information to a server; and the server for receiving an indication that the patient is to be moved to a receiving location and determining the time at which the patient should start to be moved in order to reach the receiving location when scheduled based on the tracking information.

In a feature of this aspect, the system determines the time it takes to move the patient to the receiving location. In still a further feature of this aspect, the system includes: a plurality of computing devices for receiving patient move information from the server; where the patient move information includes the start time for moving the patient; where the server further determines transport times to move from the current location of the patient to the receiving location, and schedules when the patient should start to be moved based on the transport time; where the server forwards an indication to at least one of the plurality of computing devices when the patient is going to reach the receiving location later than the scheduled time.

Broadly defined, the present invention according to one aspect is or relates to a server comprising a processor, the processor including a plurality of computer readable instructions for implementing a method for tracking patients in a medical facility, the method including: receiving an indication that the patient is to be moved to a receiving location; receiving patient tracking information from a plurality of RFID readers; and determining the time at which the patient should start to be moved in order to reach the receiving location when scheduled based on the tracking information.

In a feature of this aspect, method further includes: determining the time it takes to move the patient to the receiving location; where the method further comprises forwarding patient move information to a computing device at the receiving location, the patient move information including the start time for moving the patient; where the method further comprises determining transport times to move the patient from a current location to the receiving location, and scheduling when the patient should start to be moved based on the transport time; and/or where the method further comprises forwarding an indication to at least one of the plurality of computing devices when the patient is going to reach the receiving location later than the scheduled time.

In addition to the disclosed aspects and features of the present invention, it should be noted that the present invention further encompasses the various possible combinations and subcombinations of such aspects and features. Thus, for example, any aspect may be combined with any feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
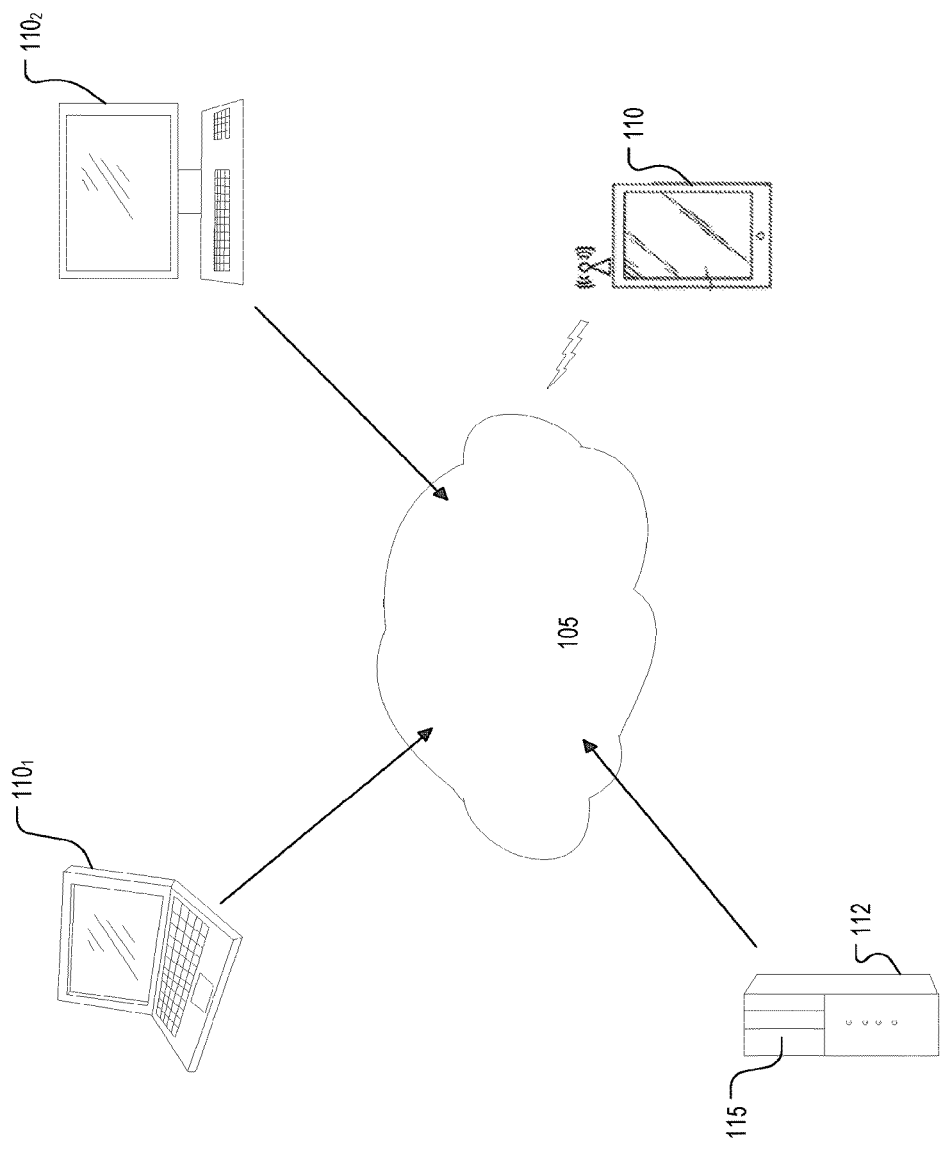
FIG. 1 illustrates an example block diagram of the disclosed system for tracking a patient in a medical facility.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

The following description of one or more preferred embodiments is merely exemplary in nature and is in no way intended to limit the invention, its implementations, or uses.

An implementation of a system and method for tracking patients/beds in a medical facility includes a graphical display of all rooms and corridors within the medical facility on one or more computing devices. This representation of the facility includes the beds that are within any of the rooms. Preferably, each patient being treated in the medical facility receives an ID band that includes a RFID chip.

An example of the disclosed tracking system 100 is illustrated in FIG. 1. The tracking system includes one or more computing devices 110$_{1 \ldots n}$, and a server 112. The computing devices 110 and the server 112 are capable of communicating with each other through a network 105, e.g., the internet or an internal network. The one or more computing devices 110 may be stationary desktops or wireless devices, e.g, tablets, laptop, smartphone, etc. The server 112 includes a processor 115.

The tracking system further includes a plurality of RFID readers (not shown), e.g., sensing antennas and interrogators, strategically located throughout the medical facility for determining the location of a patient. An example system that utilizes sensing antennas and interrogators is disclosed in U.S. Pat. No. 8,125,316.

Using an RFID chip on a patient, or bed associated with a patient, within the medical facility, periodically throughout the day, each patient's RFID tag is interrogated to confirm the patient is in their bed, or that where in the facility the patient is located. This information gathered during the periodic interrogation is forwarded to the server 112. When an order is written for a patient that requires the patient to be moved, the time the patient is to be at the location as ordered (the appointment time) is entered, and appointment information forwarded to the server 112. The processor 115 calculates the time the patient should be picked up and when the moving of the patient should begin. The processor 115 uses the tracking information stored and/or gathered, the appointment time and an estimated time it takes the patient to reach the appointment location from the patient's most recent tracked location.

Starting at a predetermined time before moving the patient should start, the patient's RFID tag would be scanned at a predetermined interval, e.g., every minute. This information is again forwarded to the server 112 and used by processor 115 to determine when the patient move has started and where along the way the patient is located.

In accordance with an alternative feature, the processor 115 may generate alerts when it appears that the patient will not arrive at the designated location on time. This alert can be used both to get the patient move started if it has not already, and to notify the receiving location that the patient could be late. An estimated time of arrival may also be provided to a computing device located at the receiving location. These alternative features could also be tied into the termination of the order processing so that transport could receive an alert that a patient was ready to be returned to his/her room.

In another implementation, the system would be able to dynamically determine transport times so that moves could be scheduled based on recent times to move a patient from point A to point B. Accordingly, a transport scheduling system could be tied into the disclosed system and method to better plan which "transporter" should pick up which patient so that patients get to tests/procedures and back to their rooms with the least amount of time spent waiting in a hallway.

Figure 2:
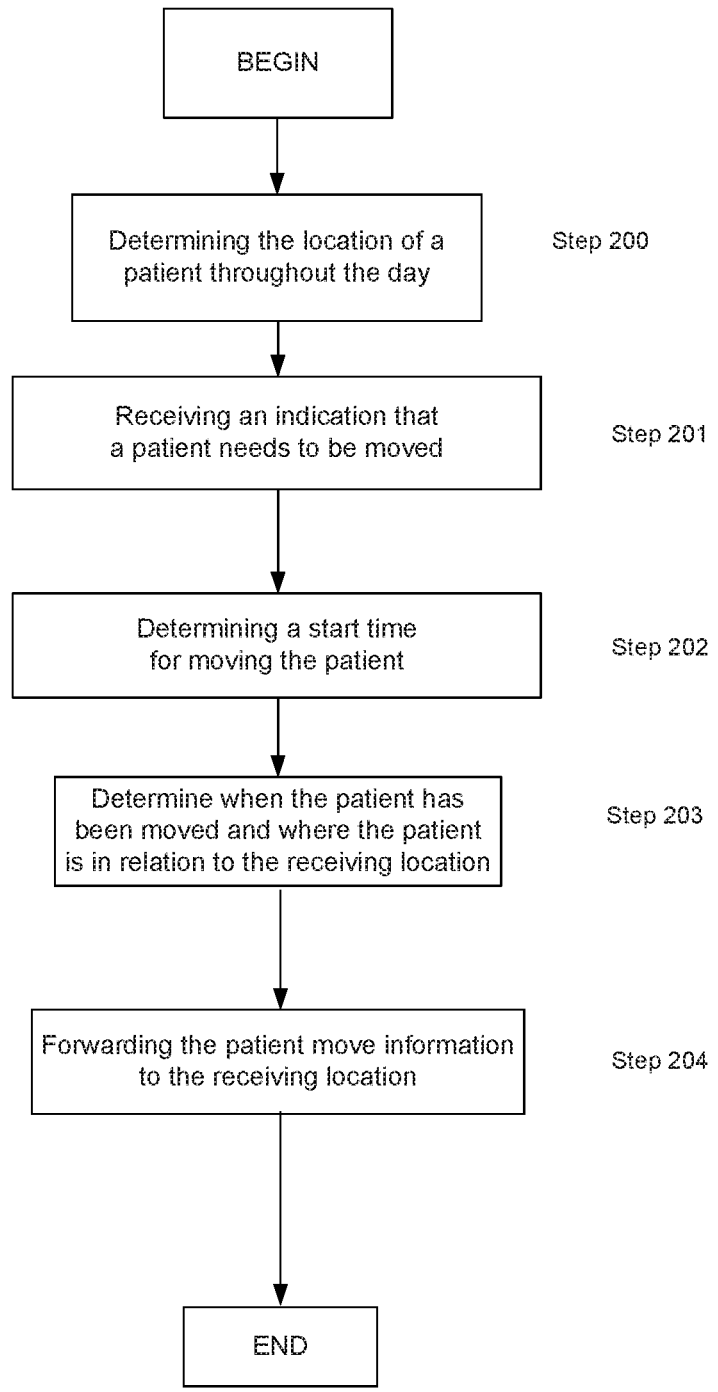
FIG. 2 illustrates an exemplary flow diagram of the method for tracking a patient in a medical facility.

An example flow diagram of the disclosed method is illustrated in FIG. 2. The location of a patient in the medical facility is periodically determined throughout the day using the patient's RFID band. Step 200. When an order is written for a patient that requires the patient to me moved, Step 201, a start time for moving the patient is determined. Step 202. On or close to the start time of the patient move, the patient's RFID is scanned at a predetermined rate to determine when the patient was moved and where the patient is in relation to the receiving location. Step 203. This information is then forwarded to the receiving location. Step 204.

The disclosed system and method reduces the time the patient spends outside of their room waiting, improves the utilization of equipment if the patients arrive on time, and helps reduce the number of people required to move patients from their rooms to the locations for tests and procedures.

Further the disclosed system and method could be used to dynamically locate a patient if the patient is delivered to the wrong location and if the patient wanders off.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for scheduling a move of a patient in a medical facility, the method comprising:
   (a) periodically interrogating, utilizing radio frequency identification (RFID) readers disposed at various locations throughout a medical facility, RFID tags secured to patients at the medical facility to monitor the location of each of the patients;
   (b) receiving, at a server, an order for a first patient to be moved to a destination location within the medical facility;
   (c) determining, at the server based on a most recent interrogation of the RFID tag secured to the first patient, a first most recent tracked location of the first patient;
   (d) determining, at the server based on the destination location and the first most recent tracked location, a first estimated travel time for the first patient to reach the destination location;
   (e) determining, at the server based on the first estimated travel time and an appointment time, a pick up time for the order;
   (f) subsequently, at a time after the determined pick up time, determining, at the server based on a most recent interrogation of the RFID tag secured to the first patient, a second most recent tracked location of the first patient;
   (g) determining, at the server based on the destination location and the second most recent tracked location, an estimated arrival time for the first patient to reach the destination location, and determining that the estimated arrival time is after the appointment time;
   (h) communicating from the server to an electronic device, based on the determination that the estimated arrival time is after the appointment time, an alert indicating that the first patient may be late to arrive at the destination location; and
   (i) displaying, on a display of the electronic device, the alert.

2. The method of claim 1, wherein periodically interrogating the RFID tags comprises periodically interrogating the RFID tags every minute.

3. The method of claim 1, wherein determining, at the server based on the destination location and the first most recent tracked location, a first estimated travel time for the first patient to reach the destination location comprises determining an estimated travel time utilizing recent historical data on the time it took to move a patient.

4. The method of claim 1, wherein the electronic device comprises a desktop.

5. The method of claim 1, wherein the electronic device comprises a laptop.

6. The method of claim 1, wherein the electronic device comprises a tablet.

7. The method of claim 1, wherein the electronic device comprises a smartphone.

8. The method of claim 1, wherein the electronic device comprises a wireless device.

9. A system comprising:
   (I) a plurality of radio frequency identification (RFID) tags each secured to a patient at a medical facility;
   (II) a plurality of RFID readers disposed at various locations throughout the medical facility;
   (III) an electronic device disposed within the medical facility;
   (IV) a server comprising one or more computer readable media containing computer executable instructions for performing a method for scheduling a move of a patient in the medical facility, the method comprising (a) periodically interrogating, utilizing the RFID readers disposed at various locations throughout the medical facility, the RFID tags secured to the patients to continuously monitor the location of each of the plurality of patients, (b) receiving, at the server, an order for a first patient of the plurality of patients to be moved to a destination location within the medical facility, the order including an appointment time at which the patient is to be at the destination location, (c) determining, at the server based on a most recent interrogation of the RFID tag secured to the first patient, a first most recent tracked location of the first patient, (d) determining, at the server based on the destination location and the first most recent tracked location, a first estimated travel time for the first patient to reach the destination location, (e) determining, at the server based on the first estimated travel time and the appointment time, a pick up time for the order, (f) subsequently, at a time after the determined pick up time, determining, at the server based on a most recent interrogation of the RFID tag secured to the first patient, a second most recent tracked location of the first patient;

(g) determining, at the server based on the destination location and the second most recent tracked location, an estimated arrival time for the first patient to reach the destination location, and determining that the estimated arrival time is after the appointment time, (h) communicating from the server to the electronic device, based on the determination that the estimated arrival time is after the appointment time, an alert indicating that the first patient may be late to arrive at the destination location, and (IV) the electronic device, the electronic device including one or more computer readable media containing computer executable instructions for performing a method involving receiving an alert communicated by the server and displaying, on a display of the electronic device disposed proximate the destination location, the received alert.

10. The system of claim 9, wherein periodically interrogating the RFID tags comprises periodically interrogating the RFID tags every minute.

11. The system of claim 9, wherein determining, at the server based on the destination location and the first most recent tracked location, a first estimated travel time for the first patient to reach the destination location comprises determining an estimated travel time utilizing recent historical data on the time it took to move a patient.

12. The system of claim 9, wherein the electronic device comprises a desktop.

13. The system of claim 9, wherein the electronic device comprises a laptop.

14. The system of claim 9, wherein the electronic device comprises a tablet.

15. The system of claim 9, wherein the electronic device comprises a smartphone.

16. The system of claim 9, wherein the electronic device comprises a wireless device.

* * * * *